United States Patent
Spengler et al.

(10) Patent No.: US 8,173,110 B2
(45) Date of Patent: May 8, 2012

(54) PRE-SHAVE PREPARATION WITH ENHANCED LUBRICITY

(75) Inventors: Eric Spengler, Ridgefield, CT (US); Teresa Petraia, Norwalk, CT (US)

(73) Assignee: Combe Incorporated, White Plains, NY (US)

( * ) Notice: Subject to any disclaimer, the term of this patent is extended or adjusted under 35 U.S.C. 154(b) by 0 days.

(21) Appl. No.: 12/954,388

(22) Filed: Nov. 24, 2010

(65) Prior Publication Data

US 2011/0070178 A1    Mar. 24, 2011

Related U.S. Application Data

(63) Continuation of application No. 11/842,700, filed on Aug. 21, 2007.

(51) Int. Cl.
*A61K 8/72* (2006.01)
*A61Q 5/00* (2006.01)

(52) U.S. Cl. ........................ 424/70.11; 424/73

(58) Field of Classification Search .................. None
See application file for complete search history.

(56) References Cited

U.S. PATENT DOCUMENTS

| | | | | |
|---|---|---|---|---|
| 4,963,352 | A * | 10/1990 | Roberts | 424/73 |
| 5,756,081 | A | 5/1998 | Wdowik | |
| 7,811,553 | B2 * | 10/2010 | O'Grady et al. | 424/73 |
| 2002/0086039 | A1 * | 7/2002 | Lee et al. | 424/401 |
| 2004/0202635 | A1 | 10/2004 | Clausen et al. | |
| 2006/0204469 | A1 | 9/2006 | Spengler et al. | |
| 2006/0269500 | A1 * | 11/2006 | Riemer et al. | 424/70.12 |
| 2008/0019936 | A1 * | 1/2008 | Wilson | 424/70.13 |
| 2008/0038218 | A1 | 2/2008 | Brun et al. | |

FOREIGN PATENT DOCUMENTS

EP        0385312 A2    9/1990

OTHER PUBLICATIONS

Phoenix Chemical Inc. Fluorosilicone Fluids (Pecosil). Aug. 2007.*
Rheology Modifiers Handbook: Practical Use and Application. Braun et al. 2000., see p. 83. http://books.google.com/books?id=65HW4HWiTWgC&printsec=frontcover&dq=rheology+modifiers+handbook+practical+use+and+application&source=bl&ots=SRcbP3OwSk&sig=rFYi9xRw9_sL7X3h4K3F5gKOXL4&hl=en&ei=ffFjTZCKIIvAgQfj4bGsAg&sa=X&oi=book_result&ct=result&resnum=4&s.*
Rohm & Haas Personal Care; The Ingredients of Creativity, "Aculyn (TM) Rheology Modifier Product Selection Guide" brochure and formulations available at www.rhpersonalcare.com, 2005, 2 pages.
Amihope LL Advertising literature, 4 pages, document created prior to filing of U.S. Appl. No. 11/842,700.
Siltech Corporation & Biosil Technologies "Biosil Basics Fluorosil 14", Issued Apr. 2005, 4 pages.
Barnett, Gabriel MS. et al. Cosmetics and Toiletries, "Electric Preshave Lotions", Jul. 1976, 2 pages.
Phoenix Chemical, Inc.; PHOENOMENON, "Fluorosilicone Fluids" www.phoenix-chem.com, retrieved from webside on Aug. 20, 2007, 4 pages.
National Institutes of Health, National Library of Medicine, Specialized Information Services, "Household Products Database", http://householdproducts.nlm.nih.gov/cgi-bin/household/brands?tbl=brands&id=16003200, retrieved from website on Sep. 17, 2005, 2 pages.
Combe Incorporated Marketing, Eleventh Edition, "International Cosmetic Ingredient Dictionary and Handbook", http://www.combe.com/aboutus.shtml, 2006, 4 pages.
Rieger, Martin M. Ph D. Harry•s Cosmeticology 8th ed., Chemical Publishing Co., Inc., 2000; 511-515.
Elsnau, Walter, "Skin Friction Measurement" CRC Press 1995, 3 pages.
Zaoui, Myriam, Malka, Eric, The Art of Shaving. Clarkson Potter/Publisers, 2002, entire book.

* cited by examiner

*Primary Examiner* — Scott Long
*Assistant Examiner* — Sarah Alawadi
(74) *Attorney, Agent, or Firm* — St. Onge Steward Johnston & Reens LLC

(57) ABSTRACT

A pre-shave composition to lubricate skin, comprising at least one polyfluoroalkyl dimethicone polymer, a volatile component to serve as a carrier to the polyfluoroalkyl dimethicone polymer, and a suspending agent to suspend the polyfluoroalkyl dimethicone polymer in the volatile component.

31 Claims, No Drawings

PRE-SHAVE PREPARATION WITH ENHANCED LUBRICITY

CROSS-REFERENCE TO RELATED APPLICATIONS

The present application is a continuation of pending U.S. patent application Ser. No. 11/842,700, filed on Aug. 21, 2007, the content of which is incorporated herein by reference.

FIELD OF THE INVENTION

This invention generally relates to cosmetic compositions, more particularly to pre-shave compositions that reduce friction between the skin surface and razor and improve the feel of the skin.

BACKGROUND OF THE INVENTION

Compositions applied to the skin prior to shaving known in the art generally seek to prepare the skin to receive a razor, providing lubrication and reducing friction to prevent irritation or cutting of the skin. With respect to preparations designed for electric shaving, typically, these compositions have the disadvantage of leaving the skin feeling greasy or oily, which is uncomfortable and unpleasant to the user.

When consumers use a pre-shave product in conjunction with an electric razor, they can sense the friction between the skin and the razor head(s). Friction can lead to uncomfortable skin irritation. But more importantly, friction between the razor head and skin will distort skin in front of the razor causing it to "bunch up" or create "a wave." This effectively changes the angle of the razor head to the beard hair being cut and thereby greatly reduces the efficiency of the shaving process.

Many have attempted to increase the lubricity of pre-shave compositions by including high oil contents therein. These compositions have the typical drawbacks of high-oil vehicles, namely leaving a residue of oil on the skin, causing the skin to feel oily or greasy, which is unpleasant or uncomfortable to the user and may require additional treatment to the skin, such as washing or wiping with an oil-reducing toner to remove any oily residue.

To reduce these undesirable effects, some pre-shave compositions incorporate plate-form powders, such as talc. Plate-form powders have the characteristic of adhering to the skin or electric razor. Other pre-shave compositions incorporate globular powders. EP Application No. 0 385 312 A2 employs globular powders, such as nylon, polystyrene, polyethylene, and polyester, which are spherical in shape. Spherical powders have a ball bearing like effect unlike plate-like powders. Globular powders are dispersed in a high alcohol vehicle, and hence, the composition must be shaken prior to use to mix the contents. While these pre-shave compositions assist in improving lubricity and reducing oil residue, there is room for improvement. One deficiency with solely focusing on lubricity is that there is not a direct correlation between improved lubricity and closeness of shaving.

What is needed is a pre-shave skin composition that provides enhanced lubricity without having an oily feeling and/or leaving an oily residue. It would be beneficial if the pre-shave skin composition were able to have a low oil content. It would also be beneficial if the pre-shave skin composition were to provide an effective, efficient and pleasing shaving experience to the user.

SUMMARY OF THE INVENTION

In an aspect of the present invention, a composition to lubricate skin during shaving comprising at least one polyfluoroalkyl dimethicone (also known as perfluorononyl dimethicone, PFD); a volatile component to serve as a carrier to said polyfluoroalkyl dimethicone; and a suspending agent to suspend the dimethicone in the volatile component, is provided.

It is another aspect of the present invention to provide a composition formulated to reduce skin friction between the electric razor and the skin surface, comprising, a polyfluoroalkyl dimethicone, an hydro-alcoholic carrier, and a hydrocolloid to suspend the polyfluoroalkyl dimethicone in the alcohol carrier, is provided.

It is further aspect of the present invention to provide a composition formulated to reduce skin friction between an electric razor and a skin surface, comprising a polyfluoroalkyl dimethicone component, a volatile component that is the base of the composition and serves as a carrier to the polyfluoroalkyl dimethicone component, and a suspending agent to suspend the polyfluoroalkyl dimethicone polymer in the volatile component. The composition is quick drying to rapidly evaporate any moisture on the face and temporarily draw moisture from hair, such as beard hair or leg hair, to stiffen the hair. This action causes the hair to become stiffer, stand erect and make it easier for a razor, such as an electric razor, to cut the hair close to the skin. Harry's Cosmeticology 8th Edition, Martin Rieger Editor, 2000, p. 511-514. Further, the composition is in the form of a gel. Still further, the polyfluoroalkyl dimethicone component lubricates the interface between the skin surface and the electric razor.

It is yet another aspect of the present invention to provide a pre-shave composition that improves the feel to the skin.

These and other aspects of the invention and its particular features and advantages will become more apparent from consideration of the accompanying description.

DETAILED DESCRIPTION OF THE INVENTION

A pre-shave composition for application to skin prior to shaving is described herein. The pre-shave composition is particularly effective for use with an electric razor by providing both improved lubricity and reduction of friction, but with low oil content, and without leaving an oily residue after electric shaving is completed. Compositions according to the present invention prepare the skin for shaving, while improving feel and look of skin after shaving, primarily by providing a preparation with a novel combination of ingredients. The composition reduces friction between the skin's surface and the razor and provides a closer shave, thus optimizing shaving performance. The invention also provides an improved feel to skin.

The composition generally comprises a polyfluoroalkyl dimethicone component and a suspending agent. The composition can further comprise a volatile component such as alcohol. Preferably the polyfluoroalkyl dimethicone component is fluorinated silicone, alkylfluorosilicone, fluorinated silicone polyether, or polyfluoroalkyl dimethicone. Most preferably the polyfluoroalkyl dimethicone component is polyfluoroalkyl dimethicone such as polyfluorononyldimethicone and the suspending agent is a hydrocolloid. Such combination achieves reduced skin friction between the razor and the skin surface, improves the feel of skin during and after shaving, and provides a closer shave.

Polyfluoroalkyl Dimethicone Component

The pre-shave composition utilizes polyfluoroalkyl dimethicone to impart lubricity. polyfluoroalkyl dimethicone polyfluoroalkyl dimethicone Suitable polyfluoroalkyl dimethicones are shown graphically in Formula 1:

Formula 1

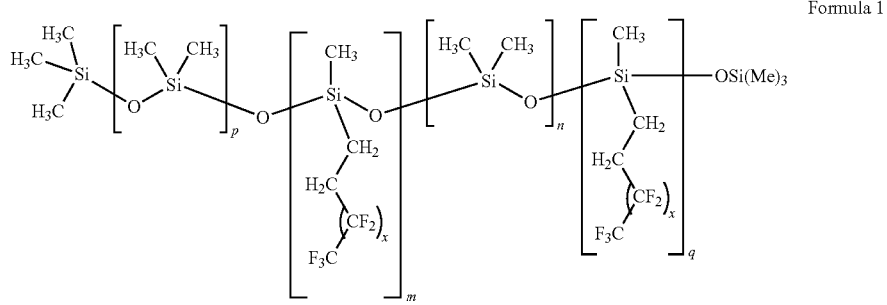

wherein x is an integer from 0 to 30, m is an integer from 1 to 40, q is an integer from 0 to 40, n is an integer from 0 to 400 and p is an integer from 0 to 200.

More preferably x is an integer from 4 to 20, m is an integer from 1 to 2, q is an integer from 0 to 2, n is an integer from 0 to 300, and p is an integer from 0 to 10.

Most preferably, x is an 6; m is 1, q is 0, n is an integer from 10 to 300, and p is 0.

Polyfluoroalkyl groups employed in the polymer generally confirm to the chemical formula: $CF_3(CF_2)_nCH_2CH_2-$, where n=6-20. Preferably, the lipophilic side chain employed is a 3, 3, 4, 4, 5, 5, 6, 6, 7, 7, 8, 8, 9, 9, 9, pentadecylfluoro nonyl group, wherein x=6 in Formula 1. Other fluorinated alkyl side chains and combinations thereof, may be used in alternatively or in combination with polyfluorononylates. In such circumstances, unsaturated polyfluoroalkenes, such as polyfluorododecene, and the like, may be employed.

With respect to the dimethicone employed in the polyfluorinated dimethicone polymer, preferably, dimethicones of molecular weights of from approximately 700 to 75000 are employed. More preferably, dimethicones of molecular weights of from approximately 1400 to 15000 are employed. These dimethicones are nonpolar and hydrophobic.

Preferably, in forming the polymer component of pre-shave composition according to the present invention, the reaction product of an anion of a polyfluoroalkyl group and a halodimethicone or polyhalodimethicone is employed. As an example, reaction of a 2-chlorosilyldimethicone with the aforementioned anion of (3,3,4,4,5,5,6,6,7,7,8,8,9,9,10,10, 11,11,12,12,12-henicosafluorododecyl)lithium would produce a polyfluoroalkyl dimethicone wherein the polyfluoroalkyl group was attached to the second silicon atom in the dimethicone polymer chain:

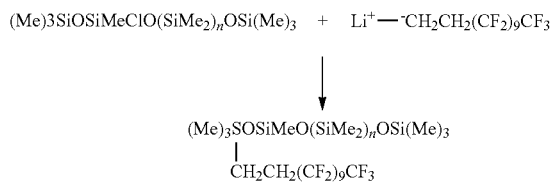

Polyfluoroalkyl dimethicones are commercially available in such products as Pecosil® FSL-150, FSL-300, FSH-150, FSH, 300, FSU-150 and FSU-300 (available from Pheonix Chemical, Inc.) and Fluorosil® D2, H418, 14, LF, J15 and 2010 (available from Siltech and from Biosil Technologies, Inc.). The characteristics of the polyfluoroalkyl dimethicones polymers impart improved lubricity to the pre-shave composition of the present invention.

Presently, use of polyfluoroalkyl dimethicones in pre-shave products is unknown. The polyfluoroalkyl dimethicone component provides the surprising effect of achieving a very smooth, soft, silky feeling.

In pre-shave compositions formulated for electric shavers, the polyfluoroalkyl dimethicone polyfluoroalkyl dimethicone component is about 0.1% to about 20% by weight, preferably about 0.5% to about 10% by weight and most preferably about 1.0% to about 5.0% by weight of total composition. These parameters ensure that the desired lubricity is achieved while not leaving an undesirable residue on the skin.

Suspending Agent

At least one suspending agent, such as a hydrocolloid, serves suspend the polyfluoroalkyl dimethicone component and is selected based upon this ability. The suspending agent can be a viscous gel.

Stokes's law defines the terminal velocity with which particles in a coarse dispersion settle. Expanding further, the equation relates to the terminal settling velocity of a smooth, rigid sphere in a viscous fluid of known density and viscosity to the diameter of the sphere when subjected to a known force field. The equation is:

$$V=(2gr^2)(d1-d2)/9\mu$$

where
V=velocity of fall (cm sec$^{-1}$),
g=acceleration of gravity (cm sec$^{-2}$),
r="equivalent" radius of particle (cm),
d1=density of particle (g cm$^{-3}$),
d2=density of medium (g cm$^{-3}$'), and
μ=viscosity of medium (dyne sec cm$^{-2}$).

The suspending agent for the pre-shave composition can be used at such a level to result in a stable preparation which will suspend the polyfluoroalkyl dimethicone component through the expected shelf life of the product. Depending on the particle size of the PFD component, this would typically mean a zero shear viscosity would be greater than about 1000 pa as measured with a TA Rheometer such as the AR550 or similar in a low shear oscillatory sweep mode. A more common form of viscosity measurement is with a Brookfield viscometer (available from Brookfield Engineering Laboratories, Inc., Middleboro, Mass.) such at the RVT, LVT or DV models. In either case the amount of hydrocolloid used would prevent coalescence or separation and would afford an even, non messy application of the pre-shave. Using the Brookfield model RVT spindle T-B @ 5 rpm, the viscosity range is about 1,000 to 300,000 centipoise and more preferably in a viscosity range from about 10,000 to about 100,000 centipoise.

In a preferred embodiment, the suspending agent is a hydrocolloid. "Hydrocolloids" or "hydrophilic colloids" are macromolecules which have a largely linear structure and have intermolecular forces of interaction which permit secondary and primary non-covalent bonds between the individual molecules and thus the formation of a reticular structure. Some are water-soluble natural or synthetic polymers which, in aqueous systems, form gels or viscous solutions. They increase the viscosity of the water by either binding water molecules (hydration) or else by absorbing and encapsulating the water into their interwoven macromolecules, at the same time as restricting the mobility of the water. Such water-soluble polymers represent a large group of chemically very different natural and synthetic polymers whose common feature is their solubility in water or aqueous media. A prerequisite for this is that the polymers contain within their chemical structures a number of hydrophilic groups sufficient for solubility in water and are not too greatly cross-linked. The hydrophilic groups may be nonionic, anionic, amphoteric or cationic in nature.

The group of the cosmetically and dermatologically relevant hydrocolloids can be divided as follows into: organic, natural compounds, such as, for example, agar agar, carrageen, tragacanth, gum arabic, alginates, pectins, polyoses, guar flour, carob bean flour, starch, dextrins, gelatins, caseine; organic, modified natural substances, such as, for example, carboxymethylcellulose and other cellulose ethers, hydroxyethylcellulose and hydroxypropylcellulose and the like; organic, completely synthetic compounds, such as, for example, polyacrylic and polymethacrylic compounds, vinyl polymers, polycarboxylic acids, polyethers, polyimines, polyamides; and inorganic compounds, such as, for example, polysilicic acids, clay minerals, such as montmorillonites, zeolites, and silicas.

Preferred hydrocolloids for the purposes of the present invention are xanthan/veegum and polyether-1, sodium carboxymethylcellulose (available under the trade name Natrosol Plus 330CS from Aqualon), the crosspolymer of methylvinylether/maleic anhydride copolymer (available under the trade name Stabileze from ISP), and other hydrocolloids adequately described in U.S. Patent Application Publications No. 2004/0202635 and 2006/0202269 A1, which are incorporated herein by reference.

Most preferably, the suspending agents are gelling agents such as polyacrylates. Advantageous polyacrylates according to the invention are acrylate copolymers and/or acrylate-alkyl acrylate copolymers, in particular those chosen from the group of so-called carbomers or carbopols (available from NOVEON Inc. under the tradenames Carbopol™ and Aqua SF-1 and from Rohm & Haas under the tradenames Aculyn™33, 22, 28, 33, 44, 46 and 88); copolymers of $C_{10-30}$-alkyl acrylates and one or more monomers of acrylic acid, or methacrylic acid or esters thereof which are crosslinked with an allyl ether of sucrose or an allyl ether of pentaerythritol (available from NOVEON Inc. under the trade names Pemulen TR1 and Pemulen TR2); polyacrylates (available from NOVEON Inc. under the tradenames Ultrez 10, 20 and 21) and others as described in U.S. Patent Application Publication No. 2004/0202635, which is incorporated herein by reference. Most preferable are polyacrylates, such as Ultrez 20 and 21, which are described in U.S. patent application 2006/0204469, which is incorporated herein by reference.

The hydrocolloid used in the present invention is preferably a polyacrylate. U.S. Pat. Appl. No. 2004/0202635, the entire disclosure of which is hereby incorporated by reference, contains an effective description of such hydrocolloids suitable for use in this invention. Of particular use are acrylate copolymers and/or acrylate-alkyl copolymers which are available under the tradenames Carbopol™ 1382, Carbopol™ 981, Carbopol™ 5984, Aqua SF-1 (Nuveon Inc.) and Aculyn™ 33 (International Specialty Products Corp.). Also useful as the hydrocolloid of the present invention are copolymers $C_{10-30}$-alkyl acrylates and one or more monomers of acrylic acid, of methacrylic acid or esters thereof which are crosslinked with an allyl ether of sucrose or an allyl ether of pentaerythritol. Additionally, compounds which carry the INCI name "acrylates/$C_{10-30}$-alkyl acrylate crosspolymer" are advantageous. Particularly advantageous are those polymers available under the tradenames Pemulen TR1 and Pemulen TR2 from NOVEON Inc. Ultrez 21 and Carbopol™ ETD 2020. Compounds which carry the INCI name acrylates/$C_{12-24}$-pareth-25 acrylate copolymer" obtainable under the tradenames Synthalen™ W2000 (from 3V Corp.), the INCI name "acrylates/steareth-20 methacrylate copolymer (as Aculyn™ 22), the INCI name "acrylates/steareth-20 itaconate copolymer" (as Structure 2001™ from National Starch, Inc.), the INCI name "acrylates/aminoacylates/$C_{10-30}$ alkyl PEG-20 itaconate copolymer" (as StructurePlus™ from National Starch) and similar polymers are useful for purposes of the present invention. The hydrocolloids preferred for use in the present invention include Carbopol™ ETD2020, Ultrez 20 and Ultrez 21.

In pre-shave compositions formulated for electric shavers, suspending agents are employed in an amount ranging from about 0.1% to about 19.0%, and preferably from about 0.3% to about 10.0% by weight.

Optionally, an appropriate neutralizer which would aid in the gelling process, such as triethanolamine, sodium hydroxide, potassium hydroxide, and tetrahydroxypropyl ethylenediamine and the like, is optionally added based upon the amount of volatile liquid that is to be gelled.

Volatile Component

When the pre-shave composition is formulated for use with electric-shavers, it is beneficial to incorporate a volatile component that serves as the base of the composition. The volatile component or liquid imparts a drying ability to the pre-shave composition. Preferable volatile liquids are those that have a vapor pressure of 60 mmHg at 300° C. or below. Examples of preferable volatile liquids used in the pre-shave preparation are standard denatured alcohol, ethanol, ethyl alcohol, cyclic or linear dimethylpolysiloxanes, a straight-chain or branched hydrocarbon and the like. Most preferably, the volatile component is ethanol or a standard denatured alcohol which uses approved denaturant such as denatonium benzoate (commercially available under the tradename Bitrex®) and tert-butyl alcohol (commercially available under the tradename SDA40B).

The content of the volatile component is at least 50% by weight, and preferably at least 70% by weight of total composition. These minimum ranges ensure desirable drying characteristics of the pre-shave composition for electric razors after application. A slower drying time can be detrimental to the convenience and speediness in use of an electric shaver. The high volatility of the liquid component hastens the evaporation of moisture on the skin. In addition, the volatile liquid partially dehydrates some of the moisture normally present in the beard. The partial dehydration has an important effect in stiffening the beard hairs, making them stand up more readily and thus permits easier cutting.

Suitable Emollient

Optionally, the preshave composition can contain a suitable emollient to soften and soothe the skin. Suitable emollients are known to those skilled in the art and include hydrocarbons, silicones, fatty alcohols, fatty acids, synthetic or natural esters, combinations thereof, and the like. Suitable emollients are useful in providing a cost effective preshave composition by reducing the amount of the polyfluoroalkyl dimethicone component necessary. Suitable emollients can be included in an amount between about 0.1% to about 8.0%, preferably in an amount ranging from about 0.5% to about 6.0%, and most preferably from about 1% to about 5.0% by weight.

Other Ingredients

Other adjunct ingredients suitable for use in this pre-shave composition include, but are not limited to, skin conditioners, humectants, color, fragrance, antioxidants, chelators, natural extracts, vitamins, UV light absorbers, opacifying agents, solvents and combinations thereof.

EXAMPLES

The following table depicts some non-limiting examples of pre-shave compositions for electric razors in accordance with the present invention:

TABLE 1

| Formulation | 1 | 2 | 3 | 4 |
| --- | --- | --- | --- | --- |
| Polyflouroalkyl Dimethicone | 2.0 | 0.6 | 2.0 | 1.0 |
| Deionized water | 16.4 | 19.8 | 14.4 | 18.4 |
| Acrylate/C10-30 Alkyl Acrylate Crosspolymer | 0.6 | 0.6 | 0.6 | 0.6 |
| Isodecyl Neopentanoate (Suitable Emollient) | 2.0 | — | 4.0 | — |
| Trimethylolpropane Triethylhexanoate (Suitable Emollient) | 1.0 | — | 1.0 | — |
| Jeesperse HD (Isodecane, Dimethicone Crosspolymer-3, Laureth-4, Ceteth-10) (Suitable Emollient) | — | 1.0 | — | 2.0 |
| SD Alcohol 40 | 78.0 | 78.0 | 78.0 | 78.0 |

The formulations 1-3 were prepared by the following method. The acylate crosspolymer was blended in water until smooth. Using moderately high shear agitation the other hydrophobic ingredients were added followed by the alcohol. Mixing was continued until the formulation was uniform.

Skin Friction Testing

Pre-shave compositions containing polyfluoroalkyl dimethicone component, and the like, impart a smooth, non-greasy feel to the shaven face and, as the following test procedures demonstrate, allow the user to achieve a closer shave with less skin friction. Formulations for pre-shave compositions used with electric razors were quantitatively evaluated for skin friction against a control formulation (isopropyl myristate, 17.0%; SD alcohol 40, 83.00%) and a test plate like powder formulation using Lauroyl Lysine (sold under the trade name of Amihope LL from Ajinomoto), alcohol, and a hydrocolloid to suspend the fatty acid/amino acid polymer powder. The control represents a currently marketed pre-shave product. The Amihope formulation was prepared in accordance with the following formula:

TABLE 2

| Amihope Formulation | % w/w |
| --- | --- |
| Deionized Water | 20.60 |
| Disodium EDTA | 0.05 |
| Acrylates/C10-30 Alkyl Aciylate Copolymer. | 0.70 |
| Glycereth-26 | 1.50 |
| Methylpropanediol | 0.70 |
| PEG-6 Caprylic Capric Triglycerides | 0.50 |
| SD Alcohol 40-B | 70.0 |
| Isosteareth-2 Octanoate | 0.50 |
| Hydrogenated Didecene | 2.75 |
| Lauroyl Lysine | 1.50 |
| Tetrahydroxypropyl Ethylenediamine | 1.20 |

Pre-shave formulations were further evaluated for closeness of shave against the control formulation and the Amihope formulation. Further, the pre-shave formulations were evaluated for overall shaving and skin feel properties based on input from an external expert panel (n=10).

Friction testing was performed on pre-shave compositions containing a perfluorononyl dimethicone (PFD) polymer. This testing utilized a skin friction meter that presses a probe against a synthetic skin surface and measures the force required to either push or pull the probe on the surface. The skin friction meter measures the coefficient of friction for each tested sample.

An instrument known as the Skin Friction Meter designed by Measurement Technologies (Cincinnati, Ohio) is available through Aca-Derm, Inc of Menlo Park, Calif. The instrument is a rotary disk instrument and consists of three main parts: a probe unit, a stationary shell and a rotary disc transducer. The probe unit consists of a small DC motor with a Teflon disk type probe attached. It is mounted inside the stationary shell between two ball bearings and is connected to the shell by a coil spring. The rotary probe transducer is mounted on the end of the stationary shell and is joined to the end of the probe unit by a soft coupling and monitors the position of the probe unit. Since the unit has a hard probe, it may be used to measure most skin friction phenomena as is.

The instrument is designed to be hand held and for maximum flexibility, is connected to its electronic controller by a six foot cable. For hand held use, the following design innovations are used to control application pressure. The instrument rests on the measurement area on a Lexan® plastic base plate which has a hole in the center. When resting on the skin surface, the application force causes the skin and underlying tissues to protrude through the hole. Application pressure on the probe itself is controlled by its position relative to the hole in the plastic base plate. Therefore, since the hole in the base plate is constant and the probe position is constant, when the measurement head rests on the measurement site with only its own weight, probe contact pressure will remain constant. In order to keep measurements within the linear range of the transducer, probe application pressure may be either increased or decreased by changing the position of the probe relative to the base plate.

The probe is adjusted to accommodate measurements which are either too low or too high. Motor speed is 69.4 rpm maximum and may be manually controlled from the front panel of the control box. The analog output of the instrument in its most linear range is a 6 volt d.c. range from −3.0 to 3.0 volts. Torque or force applied to the probe is measured and displayed as friction meter units. The higher the unit the greater the "friction value".

Friction measurements were taken using a synthetically produced "skin" called VITRO-SKIN as supplied by IMS Inc. (Orange, Conn.). The "skin" was cut into 2×2 cm squares and placed in a hydration chamber according to IMS directions. Baseline readings were taken without application of the pre-shave preparation. A determined amount of the pre-shave preparation (10 µl) was applied to the site using a micropipette and allowed to dry for 15 seconds. The probe was then placed on the site and measurements were taken after 30 and 90 sec. The latter value corresponds to an extended shaving process.

The following table identifies pre-shave PFD formulations by weight percent that underwent friction testing:

TABLE 3

| Formulation | PFD 1 | PFD 2 | PFD 3 |
|---|---|---|---|
| PFD | 2.0 | 0.6 | 2.0 |
| Deionized water | 16.4 | 19.8 | 14.4 |
| Acrylate/C10-30 Alkyl Acrylate Crosspolymer | 0.6 | 0.6 | 0.6 |
| Isodecyl Myristate | 2.0 | — | 4.0 |
| Trimethylolpropane Triethylhexanoate | 1.0 | — | 1.0 |
| Jeesperse HD | — | 1.0 | — |
| SD Alcohol 40 | 78.0 | 78.0 | 78.0 |

For each sample, a baseline coefficient of friction measurement was taken on the synthetic skin surface without a pre-shave preparation. The sample was then applied to the surface and coefficient of friction measurements were taken of the surface at 30 seconds and 90 seconds after the sample was applied. Each sample was tested three times for each period. The following table lists the average coefficient of friction measurement for the baseline, each period and the percent change in friction due to the application of each pre-shave preparation relative to the baseline:

TABLE 4

| Sample | Baseline | 30 sec | % delta | 90 Sec | % delta |
|---|---|---|---|---|---|
| Control | 6.4 | 3.1 | −51 | 3.4 | −47 |
| PFD 1 | 5.3 | 2.9 | −46 | 2.9 | −46 |
| PFD 2 | 5.0 | 3.3 | −33 | 3.4 | −33 |
| PFD 3 | 4.2 | 2.3 | −45 | 2.2 | −47 |
| Amihope Formulation | 5.0 | 3.6 | −28 | 3.7 | −37 |

Table 3 shows that, when placed in a vehicle of ethyl alcohol and water, the polyfluoroalkyl dimethicones of the present invention demonstrated a significant reduction in skin friction.

Closeness of Shave Testing

Formulation PFD 1 and the Amihope formulation were evaluated for closeness of shave using an electric shaver as determined by measurement of remaining beard hair length post-shave against a no pre-shave use. Table 5 shows the comparative results of the closeness of shave testing for these formulations:

TABLE 5

| | PFD 1 (n = 21) | Amihope formulation (n = 20) |
|---|---|---|
| % Closer Shave (reduction in beard hair length compared to no pre-shave) | 30.94 | 8.41 |
| Std. Dev. | 47.26 | 71.75 |

The results demonstrate that the PFD formulations provide a significantly closer shave relative to no use of a pre-shave and the Amihope formulation.

Ease of Shaving and Skin Smoothness

PFD 1 was further evaluated for both ease of shaving and skin smoothness with an electric shaver against not using a pre-shave composition. Results are presented in Table 6.

TABLE 6

| | % of panel who selected PFD 1 as better than no treatment (n = 21) | % of panel who selected the no treatment side as better than PFD 1 | % of panel who selected the Amihope formulation as better than no treatment (n = 20) | % of panel who selected the no treatment side as better than the Amihope formulation |
|---|---|---|---|---|
| Smoother | 62%* | 19% | 79%* | 10% |
| Easier to Shave | 71%* | 14% | 84%* | 0% |

These results demonstrate that both PFD 1 and the Amihope formulation are statistically superior for both ease of shaving and skin smoothness when using an electric razor ($p=0.05$). A comparison of the data of Table 6 and the data of Tables 4 and 5 shows that there is not a direct correlation between the perception of better shaving and the measured effectiveness of shaving. While a user of a pre-shave composition may perceive that a pre-shave composition is effective this may not necessarily be the case. PFD 1 is shown to provide an improved reduction in skin friction, a closer shave and is recognized by a user as an effective pre-shave composition.

The test results evaluating ease of shaving and smoothness of skin as presented in Table 6, in conjunction with the diminishment of skin friction (Table 4) and improved closeness of shave (Table 5), demonstrate the efficacy of the PFD inventive composition as an improved preshave formulation relative to the currently marketed control.

The combination of a polyfluoroalkyl dimethicone component, a volatile component, and a suspending agent to suspend the dimethicone in the volatile component, as described herein provides an improved pre-shave composition. This composition provides the unexpected results of an improved closeness of shaving and lubricity to satisfy the comfort needs for skin.

Although the invention has been described with reference to pre-shave preparations containing particular elements or compositions and particular relative amounts, these are not intended to exhaust all possible arrangements or features, and indeed many other modifications and variations will be ascertainable to those of skill in the art.

What is claimed is:

1. A method for shaving skin, comprising the steps of:
applying an electric razor pre-shave composition to at least an area of a skin surface comprising hair; wherein the electric razor pre-shave composition comprises at least one polyfluoroalkyl dimethicone polymer, a volatile component that serves as a carrier to said at least one polyfluoroalkyl dimethicone polymer, and a suspending agent to suspend said at least one polyfluoroalkyl dimethicone polymer in the volatile component;
said volatile component of said electric razor pre-shave composition dehydrating moisture on the skin or in hair on the skin and said at least one polyfluoroalkyl dimethicone polymer lubricating the interface between the skin and the razor;
applying an electric razor to the area of the skin surface upon which the pre-shave composition was applied; and
removing hair from the area of the skin surface with the razor; wherein said at least one polyfluoroalkyl dimethicone polymer is of Formula 1:

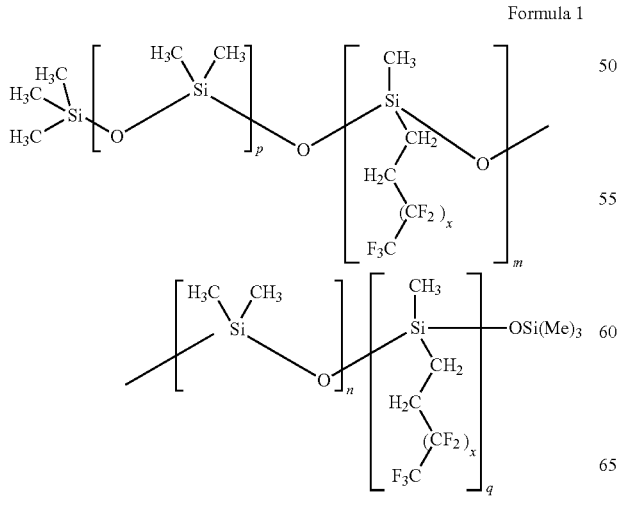

Formula 1 wherein x is an integer from 0 to 30, m is an integer from 1 to 40, q is an integer from 1 to 40, n is an integer from 1 to 200 and p is an integer from 1 to 200.

2. The method of claim 1, wherein said at least one polyfluoroalkyl dimethicone polymer is about 0.1% to about 20% by weight of the composition, the volatile component is greater than about 50% by weight of the composition, and the suspending agent is about 0.1%-19% by weight of the composition.

3. The method of claim 2, wherein said at least one polyfluoroalkyl dimethicone polymer is about 0.5% to about 10% by weight of the composition.

4. The method of claim 3, wherein said at least one polyfluoroalkyl dimethicone polymer is about 1.0% to about 5.0% by weight of the composition.

5. The method of claim 2, wherein the volatile component is about 80% of the composition.

6. The method of claim 2, wherein the suspending agent is about 0.3%-10.0% of the composition.

7. The method of claim 1, wherein the area of the skin surface is a person's face comprising beard hair.

8. The method of claim 1, wherein said at least one polyfluoroalkyl dimethicone polymer is of Formula 1 wherein, x is 6, m is 1, q is 1, n is an integer from 10 to 300 and p is 1.

9. The method of claim 1, wherein the volatile component is an alcohol.

10. The method of claim 9, wherein the suspending agent is a hydrocolloid.

11. The method of claim 10, wherein the suspending agent is a polyacrylate.

12. The method of claim 10, wherein the pre-shave composition further comprises further comprising a suitable emollient.

13. The method of claim 1, wherein the suspending agent has a viscosity of about 1,000 centipoise to about 300,000 centipoise.

14. The method of claim 13, wherein the suspending agent has a viscosity of about 10,000 centipoise to about 100,000 centipoise.

15. A pre-shave composition to lubricate the skin, comprising:
at least one polyfluoroalkyl dimethicone polymer;
a volatile component to serve as a carrier to said at least one polyfluoroalkyl dimethicone polymer, and a suspending agent to suspend said at least one polyfluoroalkyl dimethicone polymer in the volatile component and from the pre-shave composition;
wherein said at least one polyfluorononyl dimethicone polymer is of Formula 1:

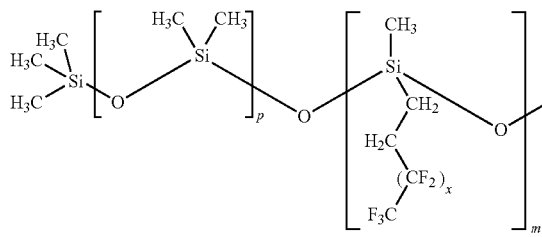
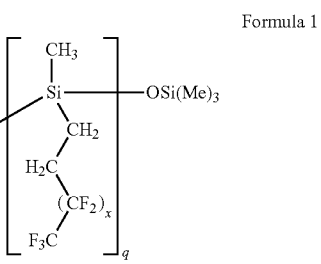

Formula 1 wherein x is an integer from 0 to 30, m is an integer from 1 to 40, q is an integer from 1 to 40, n is an integer from 1 to 200, and p is an integer from 1 to 200.

16. A composition of claim 15, wherein said at least one polyfluoroalkyl dimethicone polymer is Formula 1 wherein, X is 6, m is 1, q is 1, n is an integer from 10 to 300 and p is 1.

17. The composition of claim 15, wherein said at least one polyfluoroalkyl dimethicone polymer comprises between about 0.1% to about 20% by weight of the composition.

18. The composition of claim 17, wherein said at least one polyfluoroalkyl dimethicone polymer comprises between about 0.5% to about 10% by weight of the composition.

19. The composition of claim 18, wherein said at least one polyfluoroalkyl dimethicone polymer comprises between about 1.0% to about 5.0% by weight of total composition.

20. The composition of claim 15, wherein the volatile component comprises greater than about 50% of the total composition.

21. The composition of claim 20, wherein the volatile component comprises about 80% of the total composition.

22. The composition of claim 15, wherein the volatile component is an alcohol.

23. The composition of claim 15, wherein the suspending agent comprises about 0.1% -19.0% of the total composition.

24. The composition of claim 23, wherein the suspending agent comprises about 0.3%-10.0% of the total composition.

25. The composition of claim 15, wherein the suspending agent is a hydrocolloid.

26. The composition of claim 25, wherein the suspending agent is polyacrylate.

27. The composition of claim 15, wherein the suspending agent has a viscosity of about 1,000 centipoise to about 300,000 centipoise.

28. the composition of claim 27, wherein the suspending agent has a viscosity of about 10,000 centipoise to about 100,000 centipoise.

29. The composition of claim 15, further comprising a suitable emollient.

30. The composition of claim 15, further comprising at least one adjunct ingredient selected from the group consisting of skin conditioners, humectants, color, fragrance, antioxidants, chelators, natural extracts, vitamins, UV light absorbers, opacifying agents, solvents and combinations of these.

31. A composition to reduce skin friction, afford a closer shave and smoother skin while using an electric razor, comprising:
a polyfluoroalkyl dimethicone component;
a volatile component that is the base of the composition and serves as a carrier to the polyfluoroalkyl dimethicone component; and
a suspending agent to suspend the polyfluoroalkyl dimethicone polymer in the volatile component and form a pre-shave composition;
wherein the composition dehydrates moisture on the skin or in hair on the skin;
wherein the composition is in the form of a gel;
wherein the polyfluoroalkyl dimethicone component lubricates the interface between the skin surface and the electric razor;
wherein the polyfluoroalkyl dimethicone polymer is of Formula 1:

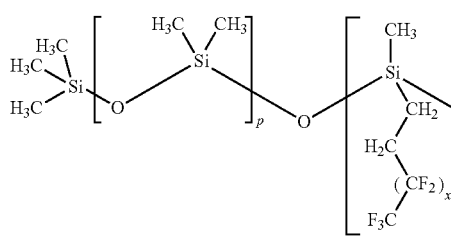
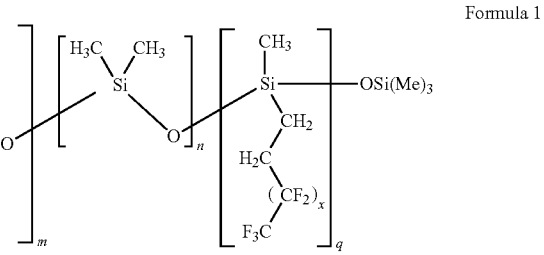

Formula 1 wherein x is an integer from 0 to 30, m is an integer from 1 to 40, q is an integer from 1 to 40, n is an integer from 1 to 200, and p is an integer from 1 to 200.

* * * * *